United States Patent [19]

Kojima et al.

[11] Patent Number: 4,469,685

[45] Date of Patent: Sep. 4, 1984

[54] PROCESS FOR PRODUCING INTERFERON INDUCERS

[75] Inventors: Yasuhiko Kojima, Yokohama; Seishi Konno; Sadao Tamamura, both of Tokyo; Takashi Hashimoto, Chofu, all of Japan

[73] Assignee: The Kitasato Institute, Tokyo, Japan

[21] Appl. No.: 491,844

[22] Filed: May 5, 1983

Related U.S. Application Data

[63] Continuation-in-part of Ser. No. 212,066, Dec. 2, 1980.

[30] Foreign Application Priority Data

Dec. 3, 1979 [JP] Japan .............................. 54-156627
Dec. 31, 1979 [JP] Japan .............................. 54-172643
Dec. 2, 1980 [EP] European Pat. Off. ........ 80304338.9

[51] Int. Cl.$^3$ .............................................. A61K 35/78
[52] U.S. Cl. .................................................. 424/195
[58] Field of Search ........................................ 424/195

[56] References Cited

U.S. PATENT DOCUMENTS 3,852,423 12/1979 Nakase et al. ...................... 424/115

OTHER PUBLICATIONS

Finter, Interferons and Interferon Inducers, pp. 13–17, 139 and 140, North–Holland Pub. Co., 1973.

*Primary Examiner*—Stanley J. Friedman
*Assistant Examiner*—John W. Rollins, Jr.
*Attorney, Agent, or Firm*—Wolder, Gross & Yavner

[57] ABSTRACT

A process for producing interferon inducers from the plants, comprising extracting a water-soluble interferon inducer with water from the tissue of a plant selected from the genera Atractylodes, Lonicera, Plantago, Lithospermum, Ligusticum, Cnidium, Bupleurum, Notopeterygium, Heracleum, Aralia, Panax, Polygala, Sophora, Euchresta, Astragalus, Sinomenium, Stephania, Cocculus, Cimicifuga, Rheum, Gastroida, Asparagus, Pinellia, Evoida and variants thereof capable of producing said interferon inducer at a temperature of from ambient to the boiling point of the extraction mixture for a period sufficient to extract the major portion of said interferon inducer present in the plant tissue, forming a supernatant, fractionating the supernatant to yield fractions containing the major portion of said interferon inducer in the supernatant and recovering said interferon inducer therefrom. Preferably, the fractionation may be effected by ultrafiltration. The interferon inducers thus obtained have a molecular weight of from about 30,000 to about 3,000,000 and are of potential interest for preventing and treating various diseases of humans and animals caused by viral infection.

15 Claims, No Drawings

PROCESS FOR PRODUCING INTERFERON INDUCERS

RELATED APPLICATION

This application is a continuation-in-part of Ser. No. 212,066 filed Dec. 2, 1980.

BACKGROUND OF THE INVENTION

This invention relates to a process for producing interferon inducers (hereinafter referred to as IF inducers) originating from the tissues of plants. Interferon, hereinafter also referred to as IF, is a substance capable of acting upon animal or human cells to inhibit the growth of a virus and is a type of protein liberated from the cell in response to viral infection. The activity of IF is specific with respect to an animal species and non-specific with respect to a viral species and may vary, with diferring conditions used for its induction. It is also known that the growth of certain animal tumour type viruses may significantly be inhibited by IF under certain conditions. A substance capable of acting upon animal or human cells to induce IF is designated as an IF inducer. Thus an IF inducer is of potential interest in the prevention and treatment of various human and animal diseases caused by viral infection. However, various known IF inducers have never been used in practice for such a purpose because of certain defects.

With regard to IF inducers originating from the plant tissues, it was known that certain mitogenic agents such as phytohemagglutinin (PHA) [Wheelock, Science, 140:310 (1965) and J. Biol. Chem., 212:607-615 (1955)], pokeweed mitogen [Friedman et al, Proc. Soc. Exp. Med., 125:90 (1967) and J. Exp. Med., 124:859-872 (1966)] and concanavalin A [Willen et al, Cell. Imminol., 6:110 (1973) and Methods of Carbohydrate Chemistry, vol. VI, 108-110 (1972)] respectively isolated from the tissues of kidney bean, poke weed and horse bean have an extremely low IF inducing activity. These mitogenic agents have been prepared by extracting the active substance with a saline solution or buffer solution from the plant tissues, treating the extracted solution with an alcohol to give a precipitate, subjecting the precipitate to column chromatography. Due to their extremely low IF-inducing activity, no successful attempt has been made to use these mitogenic agents for preventing and treating various diseases caused by viral infection. Other IF inducers orginating from the plants are also known. That is, Kojima (one of the coinventors of the present invention) et al [Japanese Patent Application as laid open to public inspection as Kokai Koho No. 32107/78] disclosed an IF inducer which is believed to be a kind of heteropolymeric saccharides containing as main constituents hexose (40%), protein (5%) and uronic acid (5%) having a molecular weight of more than 100,000. This substance is isolated from the root of *Angelica acutiloba* Kitagawa (known in Japan as Toki) by extracting the root with hot water to give an extracted solution, subjecting the same to dialysis to give a residue, adding acetone to the residue to give precipitate, followed by freeze-drying the same. If desired, the extracted solution may be made up to a suitable quantity before dialysis by concentrating in vacuo or by using a Diaflo membrane (MW=10.000). Subsequently, Kojima and Tamamura [Japanese Patent Application as laid open to public inspectionas Kokai Koho No. 99313/78] disclosed an IF inducer having a molecular weight of more than 20,000 (mainly more than 60,000) and containing as main constituents a 1-3 bonded glucose (hexose: more than 90%). This IF inducer is prepared by extracting the peeling of a mulberry e.g. *Morus alba* Linne or *M. bombycis* Koidzumi with hot water, adding an organic solvent to the extracted solution to give precipitate, adding to the same a small amount of water, subjecting the mixture to dislysis to give a residue and freez-drying the residue. If desired, the extracted solution may be made up to a suitable quantity by concentrating in vacuo or by using a Diaflo membrane. These two IF inducers are soluble in water and insoluble in organic solvents and have high IF-inducing activity.

As a result of further studies, it has been found that certain substances which we have isolated from the tissues of various higher plants show high IF-inducing activity. The present invention is based on the discovery that various plants which have been used as traditional remedies in Japan and China are not only effective in regulating general health but are also believed to be effective in curing common cold. However, there has never been any disclosure that these traditional Sino-Japanese remedies contain a substance having IF-inducing activity except the above-mentioned *Angelica acutiloba* and mulberries discovered by Japanese researchers.

We have investigated very many plants of various species and have found that certain plants are capable of producing IF-inducers. Thus, the essence of this invention resides in the selection or discovery of the plants capable of producing IF-inducers.

According to this invention, there is provided a process for producing an IF inducer, characterized in that a water-soluble IF inducer is extracted with water from the tissue of a plant selected from the genera Atractylodes, Lonicera, Plantago, Lithospermum, Ligusticum, Cnidium, Bupleurum, Notopterygium, Heracleum, Aralia, Panax, Polygala, Sophora, Euchresta, Astragalus, Sinomenium, Stephania, Cocculus, Cimicifuga, Rheum, Gastroida, Asparagus, Pinellia, Evoida and variants thereof capable of producing said IF inducers and said IF inducer is recovered from the extract thereby obtained.

The plants which may be used for the purpose of this invention are shown in the following Table 1. They are harvested usually in autumn, although, for example, the roots may be used at any time. The term "variant" used herein denotes a naturally or artificially occuring hybrid or mutant of the parent plant. Preferred plants are indicated in the following Table 2. In Table 2, the weight indicated below the item "Tissue" in the bramcket denotes a dry weight of the crude product obtained by ultrafiltration using a membrane capable of fractionating substances having a molecular weight of more than 50,000 and is calculated on the basis of 100 g (dry weight) of the plant tissue used.

In this specification, the botanical names are indicated by referring to the following publications:
(1) John D. Keys: Chinese Herbs, Their Botany, Chemistry and Pharmacodynamics (1976). pages 40-41, 56-57, 84-87, 114-115, 124-125, 136-137, 148-149, 152-153, 158-159, 178-179, 194-195, 212-213, 268-269, 290-291.
(2) Richard Hyatt: Chinese Herbal Medicine, Ancient Art and Modern Science (1978), pages 112-115, 120-127, 130-131, 134-135, 136-137, 140-141.

(3) Ohwi: Flora of Japan (1965): published by Shibundo, Tokyo in Japanese version, pages 419-420, 960-961, 1002-1003, 1368.
(4) North American Flira, vol. 24 (1926), published by The New York Botanical Garden, U.S.
(5) Illustrated Flora of the Pacific States, vol. 1, (1940), vol 2 (1950), vol. 3 (1951), vol. 4 (1965), published by The Stanford University Press, U.S.
(6) Colored Illustration of Herbaceous Plants of Japan (1980) published by Hoiku-sha, Osaka, Japan in Japanese version.
(7) Flora Europaea, vol. 2 to vol. 4 (1968), vol 5 (1976) published by Cambridge University Press, U.K.

TABLE 1

| Family (Subfamily) | Genus | Tissue* | Molecular** weight($\times 10^4$) |
|---|---|---|---|
| Compositae | Atractylodes | Rhizome | 5–100 |
| Caprifoliaceae | Lonicera | Flower | 5–100 |
| Plantaginaceae | Plantago | Seed & Leaf | 5–50 |
| Borraginaceae | Lithospermum | Root | 5–50 |
| Umbelliferaceae | Ligusticum | Root | 5–50 |
|  | Cnidium | Rhizome | 5–50 |
|  | Bupleurum | Root | 5–50 |
|  | Notopterygium | Root | 5–100 |
|  | Heracelum | Root | 5–100 |
|  | Angelica | Root | 5–100 |
| Araliaceae | Aralia | Root | 5–50 |
|  | Panax | Root | 5–50 |
| Polygalaceae | Polygala | Root | 5–50 |
| Leguminosae | Sophora | Root | 5–50 |
|  | Euchresta | Root | 5–50 |
|  | Astragalus | Rhizome | 5–100 |
| Menispermaceae | Sinomenium | Root | 5–100 |
|  | Stephania | Root | 5–100 |
|  | Cocclus | Root | 5–100 |
| Ranunclaceae | Cimicifuga | Rhizome | 5–50 |
| Polygonaceae | Rheum | Rhizome | 5–100 |
| Orchidaceae | Gastrodia | Rhizome | 5–50 |
| Liliaceae | Asparagus | Rhizome | 5–100 |
| Araceae | Pinellia | Rhizome | 5–100 |
| Rutaceae | Evoida | Fruit | 5–50 |

Notes:
*Tissue where IF inducer is rich.
**Approximate range where IF activity is prevelent.

TABLE 2

| | | | Preferred plants and IF induction in vitro and in vivo | | | |
|---|---|---|---|---|---|---|
| Example No. | (Family) Botanical name | Tissue | In vitro μg/ml | | | in vivo |
| | | | 10 | 1.0 | 0.1 | |
| | (Compositae) Atractylodes | | | | | |
| 6 | ovata DC | rhizome (1.06 g) | >100 | 88 | 30 | 05 ± 35 |
| 7 | japonica Koidz. | rhizome (1.13 g) | >100 | 92 | 45 | 45 ± 45 |
| | lancea DC | rhizome (0.98 g) | >100 | 80 | 40 | 20 ± 40 |
| | chinensis DC lancea DC var. simplicifolia Kitam. (Caprifoliaceae) Lonicera | | | | | |
| 8 | japonica Thunb. | flower (1.5 g) | >100 | >100 | 40 | 15 ± 25 |
| 9 | confusa DC | flower (1.4 g) | >100 | 90 | 35 | 10 ± 20 |
| | chinensis Watson | | | | | |
| 10 | maaeckii Maxim similis Hems tragophylla Hemsl pampaninii Levl hypoglauca Miq Macranthoides Hand-Mazz affinis Hook at Arn. flexuosa Thunb brachypoda DC chrysantha Turcz demissa Rehd morrowii A. Gray linderifolia Max strophiophora Fr. praeflorens Batalin ramosissima Fr caprifolium L. xylosteum L. sempervirens Ait (Plantaginaceae) Plantago | flower | >100 | 95 | 38 | 15 ± 30 |
| 11 | asiatica L. | seed (0.8 g) | 52 | <10 | <10 | 12 ± 12 |
| 12 | | leaf (1.3 g) | >100 | >100 | 50 | 90 ± 65 |
| 13 | patagonica | leaf (1.2 g) | >100 | >100 | 45 | 85 ± 35 |
| 14 | japonica Fr lanceolata L. | leaf (1.3 g) | >100 | >100 | 45 | 75 ± 40 |

TABLE 2-continued

Preferred plants and IF induction in vitro and in vivo

| Example No. | (Family) Botanical name | Tissue | In vitro (μg/ml) 10 | 1.0 | 0.1 | In vivo |
|---|---|---|---|---|---|---|
| | mohnikei Miq | | | | | |
| | camtschatica Cham | | | | | |
| | virginica L. | | | | | |
| | major L. | | | | | |
| | psyllium L. | | | | | |
| | loureiri Roem et Schult | | | | | |
| | (Borraginaceae) | | | | | |
| | *Lithospermum* | | | | | |
| | erythrorhizon Sieb et Zucc | root (1.1 g) | >100 | >100 | 70 | 230 ± 30 |
| | euchromum Royle | root (1.2 g) | >100 | >100 | 80 | 220 ± 35 |
| | arvense L. | | | | | |
| 17 | officinale L. | root (1.3 g) | >100 | >100 | 75 | 225 ± 40 |
| | officinale var. erythrorhizon Max | | | | | |
| | zollingeri DC | | | | | |
| | ruderale Dougl. | | | | | |
| | (Umbelliferaceae) | | | | | |
| | *Ligusticum* | | | | | |
| 18 | officinale Kitagawa | rhizome (3.2 g) | >100 | >100 | 80 | 180 ± 30 |
| 19 | chauxiong Hort | rhizome (2.8 g) | >100 | >100 | 50 | 150 ± 25 |
| 20 | wallichii Fr | rhizome (3.1 g) | >100 | >100 | 55 | 150 ± 30 |
| | japonica Max | | | | | |
| | *Cnidium* | | | | | |
| | officinale Makino | | | | | |
| 21 | japonica Miq | rhizome (3.0 g) | >100 | >100 | 55 | 160 ± 30 |
| | ajanense Drude | | | | | |
| | tachiroei Makino | | | | | |
| | *Bupleurum* | | | | | |
| 22 | falcatum L. | root (1.1 g) | >100 | >100 | 85 | 190 ± 32 |
| 23 | longiradiatum Turcz | root (1.2 g) | >100 | >100 | 64 | 160 ± 40 |
| 24 | scorzonaefolium Willd | root (1.2 g) | >100 | >100 | 55 | 150 ± 40 |
| | nipponicum Koso-Poliansky | | | | | |
| | longiradiatum var. shikotanensis Ohwi | | | | | |
| | shikotanensis Hort | | | | | |
| | triadiatum Adams | | | | | |
| | longiradiatum var. brevirsdiatum Fr. Scm | | | | | |
| | *Notopterygium* | | | | | |
| 25 | incisium Ting | root (2.2 g) | >100 | >100 | 92 | 200 ± 20 |
| | *Heracleum* | | | | | |
| | lanatum Michx | root (2.8 g) | >100 | >100 | 80 | 280 ± 40 |
| | hemsleyanum Michx | | | | | |
| | canadium Fr. | | | | | |
| | stenopterum Diels | | | | | |
| | (Araliaceae) | | | | | |
| | *Aralia* | | | | | |
| 26 | cordata Thunb | root (1.2 g) | >100 | 90 | 35 | 130 ± 28 |
| | *Panax* | | | | | |
| 27 | ginseng Meyer | root (1.2 g) | >100 | 80 | 10 | 25 ± 5 |
| 28 | japonica Meyer | root (1.4 g) | >100 | 55 | 10 | 22 ± 7 |
| | quinquefolius L. | | | | | |
| | pseudo-ginseng Wall | | | | | |
| | (Polygalaceae) | | | | | |
| | *Polygala* | | | | | |
| 29 | tenuifolia Willd | root (1.5 g) | >100 | >100 | 78 | 90 ± 20 |
| 30 | japonica Houtt | root (1.1 g) | >100 | >100 | 70 | 90 ± 20 |

TABLE 2-continued
Preferred plants and IF induction in vitro and in vivo

| Example No. | (Family) Botanical name | Tissue | In vitro (μg/ml) 10 | 1.0 | 0.1 | In vivo |
|---|---|---|---|---|---|---|
| | *tatarinowii* Regel | | | | | |
| | *reinii* Fr. et Sav | | | | | |
| | (*Legminosae*) | | | | | |
| | *Sophora* | | | | | |
| 31 | *angustifolia* Sieb et Zucc | root (2.6 g) | >100 | >100 | 85 | 120 ± 40 |
| | *angustifolia* var. *purpurascens* Makino | | | | | |
| | *flavescens* var. *angustifolia* Kitagawa | | | | | |
| 32 | *flavescens* Ait. | root (2.5 g) | >100 | >100 | 80 | 110 ± 55 |
| 33 | *subprosarata* Chun et Chun | root | >100 | >100 | 90 | 105 ± 45 |
| | *Euchresta* | | | | | |
| 34 | *japonica* Benth | root (1.3 g) | >100 | >100 | 80 | 105 ± 45 |
| | *Astragalus* | | | | | |
| 35 | *membranaceus* Bunge | rhizome (1.4 g) | >100 | >100 | 90 | 130 ± 32 |
| 36 | *mongholicus* Bunge | rhizome (1.6 g) | >100 | >100 | 80 | 120 ± 40 |
| | *adsurgens* Pall | | | | | |
| | *sinicus* L. | | | | | |
| | *reflexistipulus* Miq. | | | | | |
| | *yamamotoi* Miyake et al | | | | | |
| | *hoantchy* Fr | | | | | |
| | (*Menispermaceae*) | | | | | |
| | *Sinomenium* | | | | | |
| 38 | *acutum* Rhed et Wils | root (1.1 g) | >100 | >100 | 65 | 270 ± 30 |
| | *diversifoloium* Diels | | | | | |
| | *Stephania* | | | | | |
| 39 | *tetrandra* Moore | root (1.3 g) | >100 | >100 | 70 | 250 ± 40 |
| | *Cocculus* | | | | | |
| 40 | *trilobus* DC | root (1.1 g) | >100 | >100 | 75 | 210 ± 45 |
| | *sarmentosus* DC | | | | | |
| | *laurifolius* DC | | | | | |
| | *thunbergii* DC | | | | | |
| | (*Ranunclaceae*) | | | | | |
| | *Cimicifuga* | | | | | |
| 41 | *simplex* Wormskarl | rhizome (1.2 g) | >100 | >100 | 100 | 190 ± 40 |
| 42 | *dahurica* Max | rhizome (1.1 g) | >100 | 80 | 32 | 95 ± 20 |
| 43 | *heracleifolia* Komar | rhizome (1.2 g) | >100 | 75 | 25 | 90 ± 25 |
| | *frigida* Royle | | | | | |
| | *ternata* Miq | | | | | |
| 44 | *foetida* L. | rhizome (1.0 g) | >100 | 90 | 35 | 100 ± 20 |
| | *japonica* Thunb | | | | | |
| | *racemosa* Bart | | | | | |
| | (*Polygonaceae*) | | | | | |
| | *Rheum* | | | | | |
| 45 | *palmatum* L. | rhizome (1.5 g) | >100 | >100 | 90 | 180 ± 30 |
| 46 | *officinale* Baillon | rhizome (1.4 g) | >100 | >100 | 50 | 170 ± 30 |
| | *undulatum* L. | | | | | |
| | *laciniatum* L. | | | | | |
| 47 | *rhaponticum* L. | rhizome (1.3 g) | >100 | >100 | 60 | 160 ± 40 |
| | *pontaninii* Los-Losinsk. | | | | | |
| | *enodi* Wall | | | | | |
| | *franzenbachii* Muent | | | | | |
| | *collinianum* Baillon | | | | | |
| | *speciform* Royle | | | | | |
| | (*Orchidaceae*) | | | | | |
| | *Gastroida* | | | | | |
| 48 | *elata* Blume | rhizome (4.3 g) | >100 | >100 | 95 | 280 ± 55 |

TABLE 2-continued

Preferred plants and IF induction in vitro and in vivo

| Example No. | (Family) Botanical name | Tissue | In vitro (μg/ml) 10 | 1.0 | 0.1 | In vivo |
|---|---|---|---|---|---|---|
| | gracilis Blume | | | | | |
| | nipponica Tuyama | | | | | |
| | acerina Tanaka | | | | | |
| | confusa Hinda et Tuyama | | | | | |
| | (Liliaceae) | | | | | |
| | Asparagus | | | | | |
| 49 | lucidus Lindley | rhizome (3.5 g) | >100 | >100 | 45 | 130 ± 35 |
| 50 | officinalis L. | rhizome (3.3 g) | >100 | 95 | 40 | 120 ± 20 |
| | medeoloides Thunb | | | | | |
| | racemosus Willd | | | | | |
| | schberioides Kunth | | | | | |
| | insularis Hance | | | | | |
| | falcatus Benth | | | | | |
| | oligoclonos Max | | | | | |
| 51 | cochinchinensis Merri | rhizome (3.8 g) | >100 | >100 | 35 | 110 ± 30 |
| | (Araceae) | | | | | |
| | Pinellia | | | | | |
| 52 | ternata Breit | rhizome (4.7 g) | >100 | >100 | 60 | 140 ± 35 |
| | tripartita Schott | | | | | |
| | ternata forma angustata Makino | | | | | |
| 53 | tuberifera Tenore | rhizome (4.9 g) | >100 | >100 | 65 | 150 ± 40 |
| | (Rutaeaceae) | | | | | |
| | Evoida | | | | | |
| 54 | rutaecarpa Benth | fruit (1.4 g) | >100 | >100 | 90 | 330 ± 30 |
| | officinale Dude | | | | | |
| | daniellii Hance | | | | | |

The essence of this invention resides in the discovery or selection of plants capable of producing IF-inducers, As above-mentioned, it was previously known that mitogenic agents from kidney bean, pokeweed and horse bean show a poor IF-inducing activity and that *Angelica acutiloba* and mulberries are capable of producing IF-inducers. The known IF-inducers from plants are, in general, produced by the following steps: Extraction of plant with water, saline solution or buffer solution→forming a supernatant→fractionation of the supernatant to give a precipitate containing the major portion of the IF-inducing substance by the precipitation method using an alcohol→recovery of IF inducer by freez-drying and/or column chromatography.

As the present IF inducers are soluble in water, insoluble in organic solvents, acidic and high molecular weight substances, it is possible to obtain the desired IF-inducers by any and all known methods. For example, the extraction may be effected with a saline or buffer solution, although the extraction with water is most advantageous with respect to the cost, safety and simplicity of the operation and high purity of the resultant product. Extraction of various useful substances from plants with water are well known and have been made over many years in various countries of the world at a ratio of water to plant, for example, of 30:1 to 5:1 with respect to the extraction economy. However, it is also possible to use a convenient ratio of water to plant, if desired.

It is preferred to use the dried plant for better extraction efficiency and preservation, although it is possible to use the fresh material if desired.

The extraction may conveniently be effected at any temperature from ambient to the boiling point of the extraction mixture for a period sufficient to extract the major portion of the active material in the plant because the present IF inducer is soluble in water. Especially when the extraction is effected upon the seed, a higher temperature e.g. from 80° to 120° C. may be preferred, and in the case of tissues other than the seed a lower temperature e.g. 40° to 75° C. may be preferred. As the extraction may be effected more effectively under alkaline pH, it is preferred to adjust the pH of the water to a pH of 7 to 10 before use by using a conventional alkali such as e.g. sodium hydroxide, potassium hydroxide, ammonium hydroxide or a suitable buffer solution. When the extraction is effected at ambient temperature, the extraction may usually be effected for 1 to 5 days, which may be shortened if the extraction temperature is raised. Thus, for example, extraction may be effected for 20 minutes to 6 hours at 45° to 100° C. In this manner, it is possible to extract the major portion of the active substance contained in the plant tissue (in some cases, more than 90%). However, for example, in the cases of extraction of the plants of the genera Bupleurum, Notopterygium, Heracleum, Aralia, Polygala, Evoida, Sterllaria, Gastrodia and the like, it is preferred to extract them at a relatively higher temperature e.g. at 80°–120° C. for 1–2 hours. When the extraction is effected at room temperature with water for a longer period of time, a suitable antiseptic agent may, if desired, be added to the extracting water before use. The extraction may be effected intermittently or continuously at any convenient ratio of water to raw material used, for example, 5:1 to 20:1. As the extraction of water-soluble substance from the plant tissue with water is well known in the art, it is possible to extract the major portion of the active substance from the plant tissue without difficulty. The residue of the raw material is removed from the extracted solution in conventional manner, for example, by presseing, filtering, centrifuging and the like. After this, undesired impurities are removed from the resultant supernatant in order to allow recovery of the active substance.

Although the physico-chemical properties of the IF inducers extracted from various plants have not yet been completely clarified, they are water-soluble and are believed to be high molecular weight substances. According to one embodiment of this invention, the supernatant may be fractionated by ultrafiltration e.g. using a membrane capable of fractionating substances having a molecular weight of at least 50,000, which may be effected e.g. at a pressure of from 0.1 to 5 kg/cm$^2$. The resultant active fractions are collected, combined and freeze-dried to obtain a crude powder.

It is alternatively possible to recover the active substance from the supernatant by addition of a suitable hydrophilic organic solvent which is miscible with water and incpable of dissolving the active substance such as, e.g. methanol, ethanol, propanol, butanol, acetone and the like at an appropriate concentration (e.g. 40–90% w/v) so as to form a precipitate containing the major portion of the active substance present in the supernatant, which is then dried to give a crude powder. Instead of the organic solvents, it is also possible to use an ammonium salt such as e.g. ammonium chloride, ammonium sulfate, cethylmethylammonium bromide and the like or an inorganic metallic salt such as e.g. zinc chloride, copper chloride and the like at an appropriate concentration (e.g. 20–50% w/v) to form a precipitate which is then desalted in conventional manner, for example, by dialysis, followed by freeze-drying to obtain a crude powder.

The recovery by ultrafiltration is, in general, preferred because on one hand, it is simpler, safer and cheaper in operation and on the other hand, it avoids undesired chemical changes in the desired product. It has been found that by ultrafiltration, more than 90% of impurities such as low molecular weight plant pigments which are sometimes toxic may, in general, easily be removed. Moreover, the fractionation and recovery may be performed in one throuput step.

The resultant crude powder may, if desired, further be purified by a sutable method conventionally used for purifying water-soluble, acidic, high molecular weight substances, for example, by column chromatography using a suitable agent for gel filtration or an ion exchanger. In the former case, the elution may be effected with water, although it is possible to use a suitable buffer solution. In the latter case, the elution may be effected by using a suitable buffer solution.

Prefeered agents for gel filtration are exemplified by Sephadex G-50 to G-200, Sepharose 2B to 6B, Sephacryl S-200 or S-300 (commercial products of Pharmacia Fine Chemicals AB., Sweden), Bio-Gel P-30 to P-300, Bio-Gel A (commercial products of Bio-Rad Laboratories Ltd., U.S.), Sagavac (commercial product of Saravac Laboratories Ltd., U.K.) and the like, and preferred agents for ion exchange treatment are exemplified by DEAE Sephadex A-25 and A-50 (Cl$^-$ form), QAE Sephadex A25 and A-50 (Na$^+$ form), SP Sephadex C-25 and C-50 (Na$^+$ form), DEAE Sephacel (Cl$^-$ form), DEAE Sepharose CL-6B (Cl$^-$ form), CM Sephacel CL-6B (Na$^+$ form) (commercial products of Pharmacia Fine Chemicals AB., Sweden) and the like. It is also possible to use a suitable anion or cation exchange cellulose for the purification.

The substance thus-obtained may contain impurities to a greater or lesser degree, although its IF inducing activity may be sufficient for practical purpose. If desired, it is also possible to reduce the amount of impurities further by combining these treatments. For example, a more than 1000 fold increase in the specific activity (on the basis of the activity present in the extracted solution) may be obtained by combining the gel filtration and ion exchange treatment without difficultly.

Although the physico-chemical characteristics of the active substance obtained by the process of this invention have not yet completely clarified, they are water-soluble, acidic, high molecular weight substances. Their molecular weight ranges distribute over a very wide range of from about 30,000 to about 3,000,000, although their activities are most prevalent within the ranges shown in Table 1. The molecular weights of the active substances of this invention were determined by column chromatography using various gel filtration agents such as the series of Sepharose and Sephacryl (commercial products of Pharmacia Fine Chemicals AB., Sweden) and Bio-Gel (commercial products of Bio-Rad Laboratories Ltd., U.S.) and the like. The results were compared with the corresponding figures obtained by column chromatography using the following reference materials having identified molecular weights:

blue dextran 2000T (*$2 \times 10^6$), $\alpha_2$-macroglobulin from horse serum (*$8.2 \times 10^5$), thyroglobulin from bovine thyroid (*$6.69 \times 10^5$), catalase from bovine lever (*$2.1 \times 10^5$), aldolase from rabbit muscle (*$1.58 \times 10^5$), albumin from bovine serum (*$6.7 \times 10^4$), ovalbumin from hen eggs (*$4.3 \times 10^4$), chymotrypsinogen A from bovine pancreas (*$2.5 \times 10^4$), ribonuclease A from bovine panvreas (*$4.3 \times 10^4$) and the like [* standard molecular weight].

The following non-limiting examples illustrate the invention, in which the dried plant was used as starting material unless otherwise specified, and the IF induction and the activity of the induced IF were determined by the methods of hereinafter described exeriments. All herbs used in the examples include those imported from China, those of Japaneese origin (Bupleurum) and those available from Japanese botanical gardens.

EXAMPLE 1

*Asparagus lucidus*

The root (1 kg) was washed with water and allowed to stand in water (10 l) at room temperature for 3 days to effect extraction, followed by centrifugation using a bascket (3000 r.p.m./20 minutes) to remove the residue which was washed twice with water (each 5 l). The washing liquid was combined with the supernatant and the combined solutions were centrifuged (9000 r.p.m./20 minutes). The resultant supernatant was subjected to ultrafiltration using an ultrafilter (Model UD-6, commercial product of Bio Engineering K.K., Tokyo) with XM100A membrane (commercial product of Amicon Corpn., U.S.) for fractionating substances having a molecular weight of more than 100,000 at a pressure of 3 kg/cm$^2$. The residue was collected and freeze-dried to give a whitish powder (2.05 g), of which 1.5 g was dissolved in water (5 ml) and applied to a column (4.5×70 cm) packed with Sephadex G-200 (commercial product of Pharmacia Fine Chemicals AB., Sweden) for gel filtration. The elution was effected with water (600 ml) and the effluent was divided into fractions (each 3 ml). Fraction Nos. 28-53 were collected and combined, and the combined fractions were freeze-dried to obtain a whitish powder (205 mg). For further purification, this powder (100 mg) was dissolved in a 0.01M tris-HCl buffer solution (pH=7.0; I=0.01; 5 ml) and applied to a column (2.5×70 cm) packed with DEAE Sephadex A-50 (commercial product of Pharmacia Fine Chemicals AB., Sweden). The elution was effected with a 0.1M tris-HCl buffer solution (300 ml; pH=9.0; containing 0.5M NaCl). The effluent was divided into fractions (each 3 ml) and Fraction Nos. 25-35 were collected and combined, and the combined fractions were desalted by using a visking dialyzing tube or a Diaflo membrane (MW=10,000). After this, the solution was freeze-dried to obtain a whitish amorphous powder (67.5 mg).

The IF-inducing activity was determined as follows.

Samples of the final product were used to induce IF in the cells and serum of test animals so as to determine the activity of the IF induced by the method hereinafter described in Experiment 1. The results are shown in Tables 3 and 4, from which it is apparent that the IF-inducing activity is positive.

TABLE 3

| Concentration of sample (μg/ml) | 10 | 1.0 | 0.1 |
|---|---|---|---|
| Activity in vitro | >100 | >100 | >100 |

TABLE 4

| Activity in vivo | Time of collection of blood after administration (hours) | | | | |
|---|---|---|---|---|---|
| | 0 | 1 | 2 | 4 | 6 |
| Rabbit 1 | <10 | 100 | 350 | 60 | 15 |
| Rabbit 2 | <10 | 45 | 200 | 35 | 12 |

[Note: In this specification, "<10" denotes that the IF activity was not found.]

Table 4 indicates that by using two rabbits treated by the method of Experiment 1 as hereinafter described, a highest IF inducing activity was observed 2 hours after the administration. A similar tendency was also observed in the cases of other IF inducers originating from other plants shown in Tables 1 and 2. It has also been found that all IF inducers prepared by the process of this invention are in conformity with the widely recognized definition of an IF inducer which is apparent from hereinafter described Experiment 2.

EXAMPLE 2

Sophora angustifolia

The root (1 kg) was washed with water and allowed to stand in water (10 l) at room temperature for 2 hrs. Then the solution was adjusted to a pH of 8.5 with addition of 1N NaOH and heated at 60° C. for 2 hours to effect a further extraction. The extracted solution was treated in a similar manner to that described in Example 1 to yield a whitish powder (72.3 mg). The results shown in Tables 5 and 6 indicate that the samples of this powder showed an IF inducing activity when treated by the method of hereinafter described Experiment 1.

TABLE 5

| Concentration of sample (g/ml) | 10 | 1.0 | 0.1 |
|---|---|---|---|
| Activity in vitro | >100 | >100 | 98 |

TABLE 6

| Activity in vivo | Time of collection of blood after administration (hours) | | | | |
|---|---|---|---|---|---|
| | 0 | 1 | 2 | 4 | 6 |
| Rabbit 1 | <10 | 75 | 420 | 40 | 12 |
| Rabbit 2 | <10 | 40 | 300 | 18 | 10 |

EXAMPLE 3

Evoida rutaecarpa

The fruit (100 g) was washed with water and allowed to stand in water (one l) at room temperature for 2 hours. Then the solution was heated at 100° C. for 2 hours for a further extraction. By treating te the solution in a similar manner to that described in Example 1, there was obtained a white-yellowish powder (63.5 mg), of which IF inducing activity is shown in the following Table 9.

EXAMPLE 4

Bupleurum falcatum

The root (200 g) was washed with water and allowed to stand in water (2000 ml). The extraction was effected at room temperatuve for 2 hours. Then the solution was added with 1N NaOH to adjust to a pH of 8.5 and heated at 65° C. for 2 hours. The extracted solution was centrifuged (3000 r.p.m.) for 20 minutes using a basket. The filtrate was separated from the residue which was washed twice with water (each 250 ml) and the washing liquid was combined with the filtrate. The combined solutions were made clear by centrifugation (9000 r.p.m.) for 20 minutes. The supernatant was added with an aqueous solution of ammonium sulfate (52%; 7500 ml;×3 by volume) with agitation. The mixture was stirred at 4° C. overnight and was then centrifuged (9000 r.p.m.) for 20 minutes to collect the precipitates formed which were desalted for 3 days by dialysis using a deionized water and a celllose tube, followed by freeze-drying to yield a crude powder (3.25 g). This powder was purified in a similar manner to that described in Example 1 to obtain a whitish amorphous powder (69.2 mg). Samples of the final product were used to determine the activity of the IF induced in the cells and serum of test animals by the method of hereinafter described Experiment 1. The results shown in Tables 7 and 8 indicate that the IF-inducing activity is positive.

TABLE 7

| Concentration of sample (μg/ml) | 10 | 1.0 | 0.1 |
|---|---|---|---|
| Activity in vitro | >100 | >100 | 98 |

TABLE 8

| Activity in vivo | Time of collection of blood after administration (hours) | | | | |
|---|---|---|---|---|---|
| | 0 | 1 | 2 | 4 | 6 |
| Rabbit 1 | <10 | 40 | 290 | 35 | 10 |

TABLE 8-continued

| Activity | Time of collection of blood after administration (hours) | | | | |
|---|---|---|---|---|---|
| in vivo | 0 | 1 | 2 | 4 | 6 |
| Rabbit 2 | <10 | 46 | 330 | 13 | 10* |

*No activity was found.

EXAMPLE 5

Pinellia ternata

The rhizome (200 g) was washed with water and allowed to stand in water (2000 ml) at room temperature to effect extraction, then the extraction mixture was heated at 100° C. for 2 hours to effect further extraction. The solution (2500 ml) was treated with acetone (96%; ×2 by volume) and stirred at 4° C. overnight. After this, the solution was centrifuged (9000 r.p.m./20 minutes) to separate off the residue which was dried in vacuo to give a crude powder colored in brown (2.85 g). This powder was treated in a similar manner to that described in Example 1 to obtain a whitish powder (58.5 mg). The results are shown in Table 9.

TABLE 9

| Example No. | IF activity in vitro | | |
|---|---|---|---|
| | Concentration of sample (μg/ml) | | |
| (Plant) | 10 | 1.0 | 0.1 |
| 3 (Evoida rutaecarpa) | >100 | >100 | 90 |
| 5 (Pinellia ternata) | >100 | >100 | 85 |

EXAMPLES 6-54

Various plant tissues (each 0.1 kg) listed in Table 2 were independently washed with water and allowed to stand in water (one l) at room temperature for 2 hours. Then the solution was heated at 100° C. for 2 hours to effect a further extraction. The supernatant of the extracted solution was subjected to ultrafiltration using a membrane for fractionating substances having a molecular weight of more than 50,000 (UK50, commercial product of Toyo Roshi K.K., Tokyo). The residue was treated in a similar manner to that described in Example 1 to effect gel filtration, followed by freeze-drying. The IF inducing activity was determined by the method of hereinafter described Experiment 1. In this case, two rabbits were used to determine the activity of IF induced in the serum. The activity was determined 2 hours after administration of the sample to the test animals. The results are shown in the foregoing Table 2.

EXPERIMENT 1

IF induction with IF inducer and IF assay

[Reference: Y. Kojima's report in Kitasato Arch. Exp. Med., 43:35 (1970)]

(A) IF induction in vitro

A rabbit [weight about 1 kg; New Zealand White; SPF] was sacrificed by cardic puncture and its spleen, bone marrow and lymph node cells were collected and mixed together to prepare a cell suspension ($10^7$ cells/ml) which was divided into small fractions (each 1 ml). 10, 1.0 and 0.1 μg/ml of the sample of the IF inducer to be determined were independently added to the fraction on each occasion. The mixture was cultured at 25° C. for 24 hours, followed by centrifugation (9000 r.p.m./20 minutes) to separate a supernatant which was used to determine the IF activity induced by the sample of the IF inducer.

(B) IF induction in vivo

A sample of the IF inducer was dissolved in water (500 μg/ml) and injected into the auricular vein of a rabbit (weight about 1 kg; New Zealand White; SPF). 1, 2, 4 and 6 hours after administration, a 2 ml sample of blood was removed on each occasion from the test animal and the serum of each blood sample was isolated and used as a sample for determining the activity of the IF induced in the serum.

(C) Determination of IF activity induced by IF inducer

In both methods (A) and (B), Vesicular stomatitis virus was used as the challenge virus for determining the activity of the IF induced by IF inducer. A monolayer culture of the lined cells of RK13 of rabbit was put in a dish, to which a predetermined amount of the solution obtained by the method (A) or (B) was added. The culture was incubated at 37° C. overnight. Then, Vesicular stomatitis virus was inoculated to the culture and the incubation was further effected at 37° C. overnight. In order to calculate the activity of the IF induced by IF inducer, the unit of the IF activity was expressed by the reciprocal number of the highest dilution of the sample required for reducing the number of the plaques to 50%.

EXPERIMENT 2

Definition of IF and identification of IF inducer

The active substances prepared by the abovementioned methods (A) and (B) shared the properties generally attributed to interferon such as the sensitivity to inactivation by 0.08% trypsion after reaction at 37° C. for 2 hours, inhibition of Vesicular stomatitis virus and Vaccinia virus in RK13 rabbit cell culture and absence of antiviral activity against Vesicular stomatitis virus in L cells of mouse.

The method of the above-mentioned Experiment 1 (C) is the socalled plaque reduction method which is one of the standard methods for assaying IF induced and the definition of IF indicated in Experiment 2 is the classical defintion which is also disclosed in U.S. Pat. No. 3,669,222 (1972) to A. Issac and J. Lindeman, the namers of interferon. The method of Experiments 1 and 2 are one of the standard methods used by Japanese researchers (for example, U.S. Pat. Nos. 3,852,423; 4,079,126 etc.). Thus, it is apparent that IF inducers are isolated from various plants disclosed in this specification.

What is claimed is:

1. A process for producing a water-soluble interferon inducer from a plant tissue, comprising extracting said interferon inducer with water from the tissue of a plant belonging to the group consisting of Atractylodes, Lonicera, Plantago, Lithospermum, Liqusticum, Cnidium, Bupleurum, Notopterygium, Heracleum, Aralia, Panax, Polygala, Sophora, Euchresta, Astragalus, Sinomenium, Stephania, Cocclus, Cimicifuga, Rheum, Gastroida, Asparagus, Pinellia and Evoida containing said interferon inducer at a temperature of from ambient to the boiling point of the extraction mixture for a period of up to 5 days sufficient to extract the major portion of said interferon inducer present in said tissue, forming a supernatant from the extracted solution, fractionating the supernatant to yield fractions containing the major portion of said interferon inducer present in the supernatant, and recovering said interferon inducer therefrom.

2. The process of claim 1, wherein the plant is selected from *Atractylodes ovata, Astractylodes japonica, Atractylodes lancea, Atractylodes chinensis, Atractylodes lancea var. simpllicifolia, Lonicera japonica, Lonicera confusa, Lonicera chinensis, Lonicera maaeckii, Lonicera simillis, Lonicera tragophylla, Lonicera pampaninii, Lonicera hypogolauca, Lonicera macranthoides, Lonicera affinis, Lonicera flexuosa, Lonicera brachypoda, Lonicera chrysantha, Lonicera demissa, Lonicera morrowii, Lonicera linderifolia, Lonicera strophiophora, Lonicera praeflorens, Lonicera ramosissima, Lonicera caprifolium, Lonicera xylosteum, Lonicera sempervirens, Plantago asiatica, Plantago patagonica, Plantago japonica, Plantago lanceolata, Plantago mohnikei, Plantago camtschatica, Plantago virginica, Plantago major, Plantago psyllium, Plantago loureiri, Lithospermum erythrorhizon, Lithospermum euchromum, Lithospermum arvense, Lithospermum officinale, Lithospermum officinale var. erythrorhizon, Lithospermum zolligeri, Lithospermum ruderale, Ligusticum officinale, Ligusticum chauxiong, Ligusticum wallichii, Ligusticum japonica, Cnidium officinale, Cnidium japonica, Cnidium ajanense, Cnidium tachiroei, Bupleurum falcatum, Bupleurum longiradiatum, Bupleurum scorzonaefolium, Bupleurum nipponicum, Bupleurum shikotanensis, Bupleurum longiradiatum var. shikotanensis, Bupleurum triadiatum, Bupleurum longiradiatum var. brevirsdiatum, Notopterygium incisium, Heracleum lanatum, Heracleum hemsleyanum, Heracleum canadium, Heracleum stenopterum, Aralia cordata, Panax ginseng, Panax japonica, Panax quinquefolius, Panax pseudo-ginseng, Polygala tenuifolia, Polygala japonica, Polygala tatarinowii, Polygala reinii, Sophora augustifolia, Sophora angustifolia var. purpurascens, Sophora flavescens, Sophora flavescens var. augustifolia, Sophora subprosarata, Eucresta japonica, Astragalus membranaceous, Astragalus mongholicus, Astragalus adsurgens, Astragalus sinicus, Astragalus reflexistpulus, Astragalus yamamotoi, Astragalus hoanchy, Sinomenium acutum, Sinomenium diversifolium, Stephania tetrandra, Cocculus trilobus, Cocculus sarmentosus, Cocculus laurifolius, Cocculus thunbergii, Cimicifuga simplex, Cimicifiga dahurica, Cimicifuga heracleifolia, Cimicifuga frigida, Cimicifuga ternata, Cimicifuga foetida, Cimicifuga japonica, Cimicifuga racemosa, Rheum palmatum, Rheum officinale, Rheum undulatum, Rheum laciniatum, Rheum rhaponticum, Rheum pontaninii, Rheum enodi, Rheum franzenbachii, Rheum collinianum, Rheum speciform, Gastrodia elata, Gastrodia gracillis, Gastrodia nipponica, Gastrodia acerina, Gastrodia confusa, Asparagus lucidua, Asparagus officinale, Asparagus medeoloides, Asparagus recemosus, Asparagus schberioides, Asparagus insularis, Asparagus falcatus, Asparagus oligoclonos, Asparagus cochinensis, Pinellia ternata, Pinellia tripartita, Pinellia ternata forma angustata, Pinellia tuberifera, Evoida rutaecarpa, Evoida officinale, Evoida daniellii* and variants thereof.

3. The process of claim 1, wherein the plant is a dried plant.

4. The process of claim 1, wherein the extraction is effected under alkaline conditions.

5. The process of claim 4, wherein the extraction is effected at a pH of from 7 to 10.

6. The process of claim 1, wherein the extraction is effected at a temperature of from 40° to 100° C. for 30 minutes to 6 hours.

7. The process of claim 1, wherein the fractionation is effected by ultrafiltration.

8. The process of claim 7, wherein the ultrafiltration is effected by using a membrane for fractionating substances having a molecular weight of more than 50,000.

9. The process of claim 1, wherein the fractionation is effected by adding to the supernatant an organic colvent which is miscible with water and incapable of dissolving said interferon inducer to form a precipitate containing the major portion of said interferon inducer present in the supernatant.

10. The process of claim 9, wherein the organic solvent is selected from methanol, ethanol, propanol, butanol, acetone and a mixture thereof at a concentration of 40–90% w/v.

11. The process of claim 1, wherein the fractionation is effected by adding to the supernatant one member selected from ammonium salts and inorganic metallic salts to form a precipitate containing the major portion of said interferon inducer present in the supernatant.

12. The process of claim 11, wherein said ammonium salt is selected from ammonium chloride, ammonium sulfate and cetylmetylammoniumbromide at a concentration of 20–5% w/v.

13. The process of claim 11, wherein said inorganic metallic salt is selected from zinc chloride and copper chloride at a concentration of 20–50% w/v.

14. The process of claim 1, wherein said interferon inducer has a molecular weight of from about 30,000 to about 3,000,000.

15. An amorphous whitish powder effective as an interferon inducer produced by the process of claim 1.

* * * * *